US010420917B2

United States Patent
Rosenberg et al.

(10) Patent No.: US 10,420,917 B2
(45) Date of Patent: *Sep. 24, 2019

(54) SYSTEMS AND METHODS FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US); Andrew T. Forsberg, Plymouth, MN (US); Michael W. Augustine, St. Michael, MN (US); Kim Jorgensen, Minneapolis, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,312

(22) Filed: Apr. 21, 2017

(65) Prior Publication Data

US 2017/0216562 A1 Aug. 3, 2017

Related U.S. Application Data

(63) Continuation of application No. 15/176,638, filed on Jun. 8, 2016, now Pat. No. 9,662,475, which is a continuation of application No. 13/886,343, filed on May 3, 2013, now Pat. No. 9,381,321.

(51) Int. Cl.
*A61M 25/02* (2006.01)

(52) U.S. Cl.
CPC ....... *A61M 25/02* (2013.01); *A61M 2025/028* (2013.01); *A61M 2025/0286* (2013.01)

(58) Field of Classification Search
CPC .................................................... A61M 25/02
See application file for complete search history.

(56) References Cited

U.S. PATENT DOCUMENTS

| 3,039,468 A | 6/1962 | Price |
| 3,765,032 A | 10/1973 | Palma |
| 3,856,009 A | 12/1974 | Winnie |
| 3,896,527 A | 7/1975 | Miller et al. |
| 3,938,529 A | 2/1976 | Gibbons |
| 4,043,346 A | 8/1977 | Mobley et al. |

(Continued)

FOREIGN PATENT DOCUMENTS

| WO | WO 1991/15254 | 10/1991 |
| WO | WO 2004/026152 | 4/2004 |

(Continued)

OTHER PUBLICATIONS

Web Page Printout of Statlock Device, publicly available before May 3, 2013, 2 pages.

(Continued)

*Primary Examiner* — Edelmira Bosques
(74) *Attorney, Agent, or Firm* — Fish & Richardson P.C.

(57) ABSTRACT

Some embodiments of a medical device anchor system include an anchor device that secures a medical instrument (such as a catheter or the like) in place relative to a skin penetration point using subcutaneous anchors. In some implementations, the medical instrument can be coupled to the anchor device using a snap-lock cap mechanism.

20 Claims, 10 Drawing Sheets

(56) References Cited

U.S. PATENT DOCUMENTS

| | | |
|---|---|---|
| 4,114,618 A | 9/1978 | Vargas |
| 4,164,943 A | 8/1979 | Hill et al. |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,810 A | 1/1991 | Semrad |
| 5,041,085 A | 8/1991 | Osborne et al. |
| 5,067,957 A | 11/1991 | Jervis |
| 5,122,122 A | 6/1992 | Allgood |
| 5,190,546 A | 3/1993 | Jervis |
| 5,256,146 A | 10/1993 | Ensminger et al. |
| 5,267,960 A | 12/1993 | Hayman et al. |
| 5,279,564 A | 1/1994 | Taylor |
| 5,312,337 A | 5/1994 | Flaherty et al. |
| 5,344,439 A | 9/1994 | Otten |
| 5,368,017 A | 11/1994 | Sorenson et al. |
| 5,378,239 A | 1/1995 | Termin et al. |
| 5,456,671 A | 10/1995 | Bierman |
| 5,496,277 A | 3/1996 | Termin et al. |
| 5,578,013 A | 11/1996 | Bierman |
| 5,597,378 A | 1/1997 | Jervis |
| 5,599,311 A | 2/1997 | Raulerson |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,800,402 A | 9/1998 | Bierman |
| 5,810,781 A | 9/1998 | Bierman |
| 5,814,065 A | 9/1998 | Diaz |
| 5,827,230 A | 10/1998 | Bierman |
| 5,833,664 A | 11/1998 | Seare, Jr. |
| 5,833,667 A | 11/1998 | Bierman |
| 5,857,999 A | 1/1999 | Quick et al. |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,989,265 A | 11/1999 | Bouquet De La Joliniere et al. |
| 6,213,979 B1 | 4/2001 | Bierman |
| 6,290,676 B1 | 9/2001 | Bierman |
| 6,361,523 B1 | 3/2002 | Bierman |
| 6,413,240 B1 | 7/2002 | Bierman et al. |
| 6,447,485 B2 | 9/2002 | Bierman |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,663,600 B2 | 12/2003 | Bierman et al. |
| 6,679,851 B2 | 1/2004 | Burbank et al. |
| 6,695,861 B2 | 2/2004 | Rosenberg et al. |
| 6,770,055 B2 | 8/2004 | Bierman et al. |
| 6,896,665 B2 | 5/2005 | Picha et al. |
| 6,958,044 B2 | 10/2005 | Burbank et al. |
| 7,056,286 B2 | 6/2006 | Ravenscroft et al. |
| 9,381,321 B2 | 7/2016 | Rosenberg et al. |
| 9,662,475 B2 | 5/2017 | Rosenberg et al. |
| 2002/0068898 A1 | 6/2002 | McGucklin, Jr. et al. |
| 2002/0068899 A1 | 6/2002 | McGucklin, Jr. et al. |
| 2002/0120250 A1 | 8/2002 | Altman |
| 2002/0165489 A1 | 11/2002 | McGucklin, Jr. et al. |
| 2005/0043685 A1 | 2/2005 | Schinkel-Fleitmann |
| 2005/0187578 A1 | 8/2005 | Rosenberg et al. |
| 2005/0256459 A1 | 11/2005 | Howard et al. |
| 2006/0079845 A1 | 4/2006 | Howard et al. |
| 2006/0129134 A1 | 6/2006 | Kerr |
| 2007/0021685 A1 | 1/2007 | Oepen et al. |
| 2007/0106330 A1 | 5/2007 | Rosenberg et al. |
| 2007/0225651 A1 | 9/2007 | Rosenberg et al. |
| 2009/0326470 A1 | 12/2009 | Rosenberg et al. |
| 2010/0016801 A1* | 1/2010 | Rosenberg ............ A61M 25/02 604/174 |
| 2010/0204656 A1 | 8/2010 | Rosenberg et al. |
| 2012/0078191 A1* | 3/2012 | Rosenberg ............ A61M 25/02 604/175 |
| 2012/0271238 A1 | 10/2012 | Rosenberg et al. |
| 2013/0072875 A1 | 3/2013 | Rosenberg et al. |

FOREIGN PATENT DOCUMENTS

| | | |
|---|---|---|
| WO | WO 2005/039419 | 5/2005 |
| WO | WO 2005/102438 | 11/2005 |
| WO | WO 2010/059714 | 5/2010 |
| WO | WO 2014/127010 | 8/2014 |

OTHER PUBLICATIONS

Johnson & Johnson web page printout, "The EndoANCHOR Comparative Summary" printed Sep. 13, 2005, 2 pages.

Johnson & Johnson web page printout, "The EndoANCHOR Features and Benefits" printed Sep. 13, 2005, 2 pages.

Johnson & Johnson web page printout, "The EndoANCHOR Firing Sequences" printed Sep. 13, 2005, 2 pages.

Invitation to Pay Additional Fees for PCT/US2014/36504 dated Mar. 19, 2015, 3 pages.

International Preliminary Report on Patentability for PCT/US2014/0365004, dated Nov. 12, 2015, 7 pages.

European Search Report for Application No. 14791316.4, dated Dec. 1, 2016, 4 pages.

European Communication Pursuant to Article 94(3) for Application No. 14791316.4, dated Dec. 8, 2016, 12 pages.

International Search Report for PCT/US2014/036504 dated May 28, 2015, 12 pages.

* cited by examiner

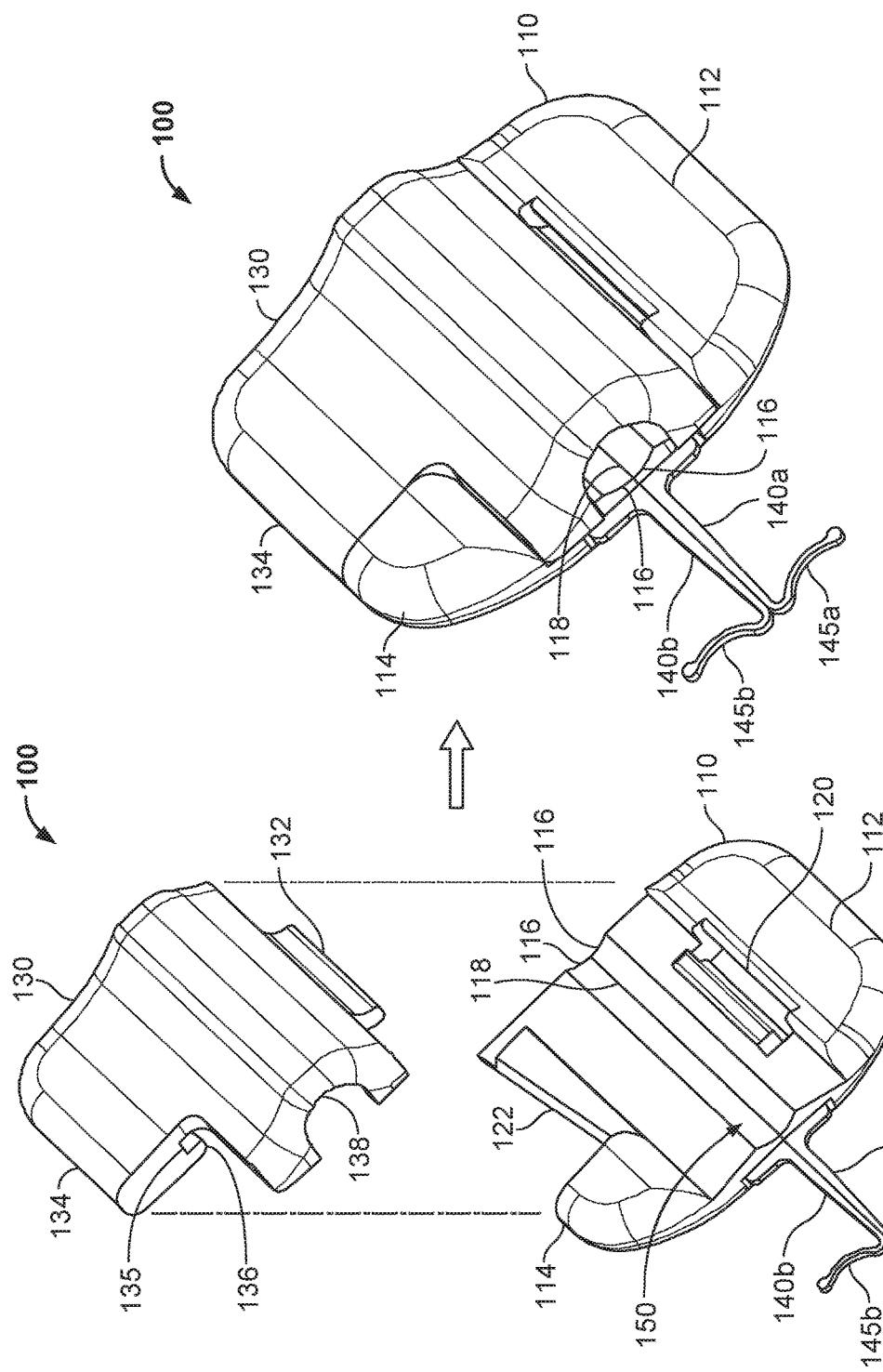

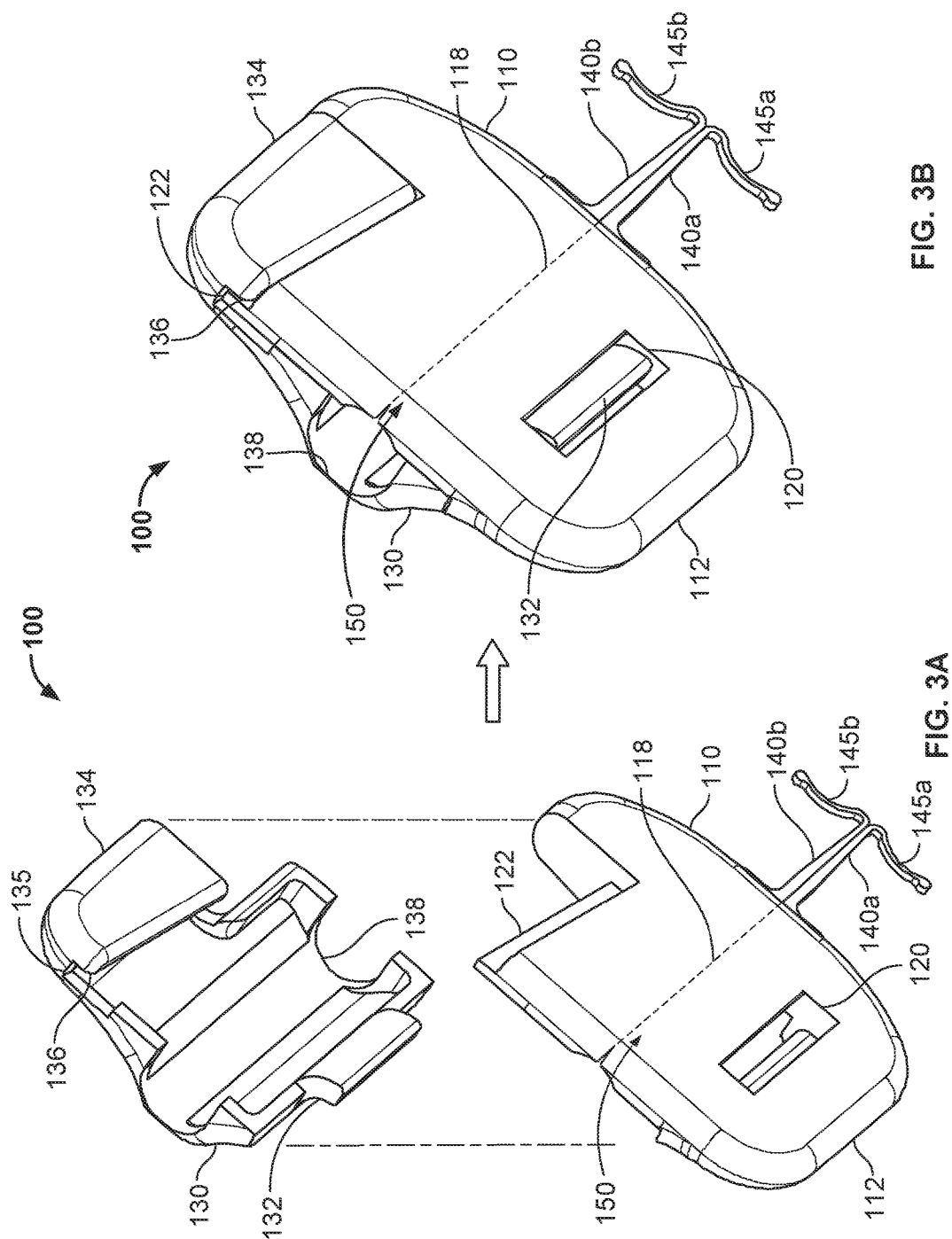

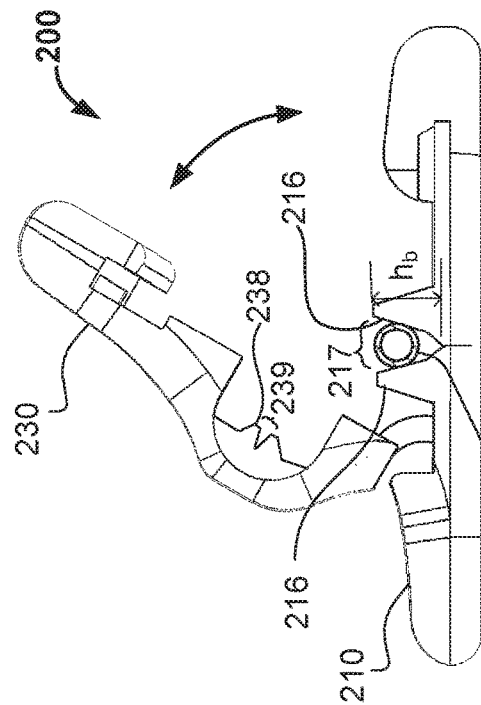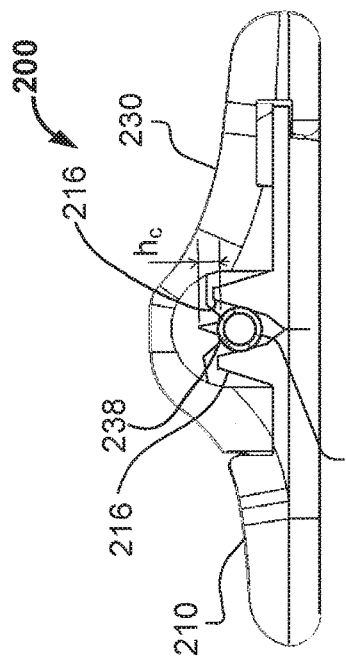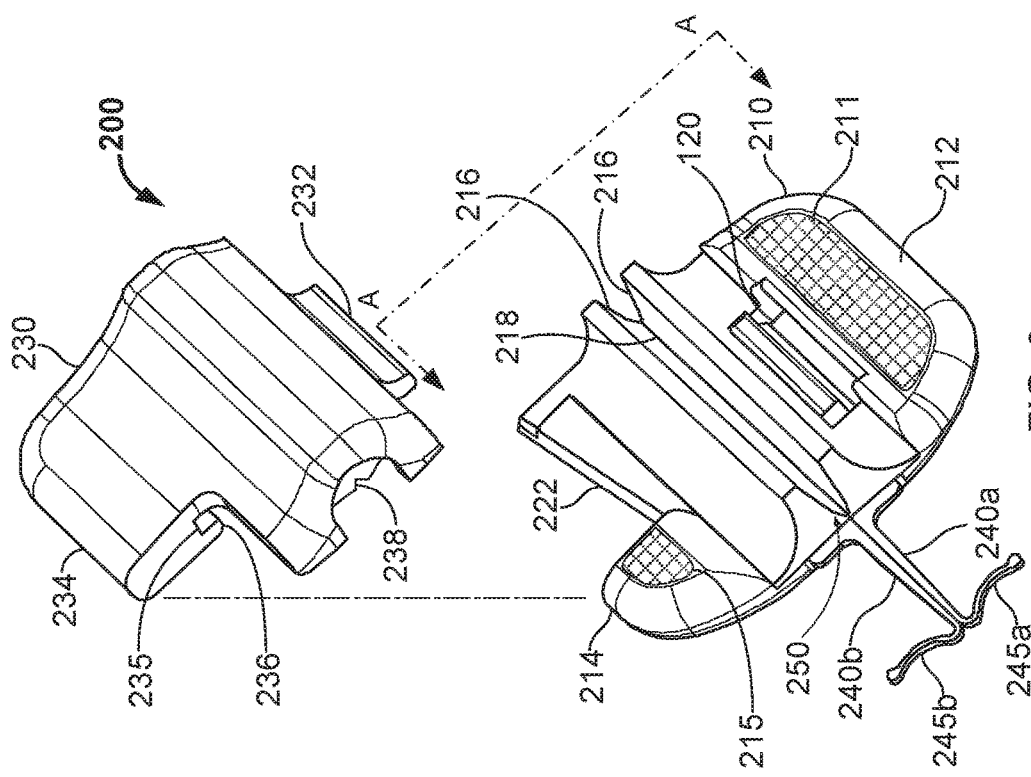

SYSTEMS AND METHODS FOR ANCHORING MEDICAL DEVICES

PRIORITY CLAIM OF PRIORITY

This application is a continuation of U.S. patent application Ser. No. 15/176,638 filed on Jun. 8, 2016, which is a continuation of U.S. patent application Ser. No. 13/886,343, filed on May 3, 2013, the entire contents of which are hereby incorporated by reference.

TECHNICAL FIELD

This document relates to a system and method for securing the position of a catheter or another medical instrument, for example, at a skin opening.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In some instances, the catheter is commonly secured to the patient using an adhesive tape on the skin or by suturing a catheter hub to the patient's skin. In other circumstances, the catheter may be secured to the patient using a subcutaneous anchor mechanism (such as an anchor sleeve or other device equipped with anchors for securing into a subcutaneous region under the skin).

SUMMARY

Some embodiments of a medical device anchor system provided herein include an anchor device configured to readily and releasably couple with a medical instrument (such as a catheter or the like) in a simplified manner. In use, the anchor device can secure the medical instrument in place relative to a patient's skin penetration point. In some implementations, the one or more subcutaneous anchors are deployed through the skin penetration point that is already occupied by the medical device, and into a subcutaneous region (e.g., the region immediately under the skin and between the skin and underlying muscle tissue which may be occupied by fatty tissue). This anchoring system can thereby reduce or eliminate the need for suturing or adhering the medical device to the patient's skin. In some embodiments, the anchor devices include a releasable cap by which the medical instrument can be conveniently coupled to the anchor device. Optionally, particular embodiments of the cap may be engaged with the base of the anchor device and positively snapped into the proper latched position using a single hand.

Particular embodiments described herein include an anchor device for securing the position of a medical instrument. The anchor device may include first and second anchors each having a longitudinal shaft portion and a tine disposed at a distal region of the longitudinal shaft portion. At least a portion of the first and second anchors can be configured to be deployed through a skin penetration point and into a subcutaneous region along an underside of a skin layer. The anchor device may further include a retainer base coupled to the first and second anchors and configured to engage an external portion of a medical instrument occupying the skin penetration point. The retainer base may include an elastically flexible folding region about which the retainer base is adjustable between a first position and a folded position. When the retainer base is adjusted to the folded position, the tines of the first and second anchors are oriented generally adjacent to each other and extend in substantially the same direction. The longitudinal shaft portion of each of the first and second anchors may extend distally from a distal end of the retainer base. The anchor device may also include a cap that is releasably attachable with the retainer base so as to define a channel therebetween that is sized to engage with the external portion of the medical instrument when the cap and the retainer base are in a first arrangement. Optionally, the cap is removable from the medical instrument when the cap and the retainer base are in a second arrangement. Also, the cap is optionally configured to pivot in relation to the retainer base during adjustment between the first arrangement and the second arrangement.

In some embodiments described herein, a method of using a medical anchor system may include advancing an anchor device toward a skin penetration point of a user while the anchor device is in a folded condition so that a plurality of subcutaneous tines of the anchor device are generally adjacent to each other and oriented to extend in substantially the same direction. The method may also include inserting the subcutaneous tines through the skin penetration point and into a subcutaneous region adjacent to an underside of a skin layer while the anchor device is in the folded condition. The method may further include adjusting the anchor device to a non-folded condition after the subcutaneous tines are inserted into the subcutaneous layer so that subcutaneous tines are in an anchored position in which the subcutaneous tines extend generally away from one another. The method may also include securing a medical instrument to the anchor device after the subcutaneous tines are adjusted to the anchored position. Optionally, the securing step includes pivoting a cap of the anchor device in relation to a retainer body of the anchor device to thereby apply a frictional force to an external portion of the medical instrument. In such circumstances, the medical instrument may be received in a channel that is defined between the cap and the retainer body.

Additional embodiments described herein include an anchor device for securing the position of a medical instrument. The anchor device may include one or more anchors each having a longitudinal shaft portion and a tine disposed at a distal region of the longitudinal shaft portion. At least a portion of the one or more anchors may be configured to be deployed through a skin penetration point and into a subcutaneous region along an underside of a skin layer. The anchor device may also include a retainer base coupled to the first and second anchors and configured to engage an external portion of a medical instrument occupying the skin penetration point. The anchor device may include a cap that is releasably attachable with the retainer base so as to define a channel therebetween that is sized to engage with the external portion of the medical instrument when the cap and the retainer base are in a first arrangement. Optionally, a first connector defines a pivotable connection between the cap and the retainer base and a second connector that is spaced apart from the first connector optionally defines a snap fit connection between the cap and the retainer base.

In some embodiments for an anchor device for securing the position of a medical instrument, the anchor device may include one or more anchors each having a longitudinal shaft portion and a tine disposed at a distal region of the longitudinal shaft portion. At least a portion of the one or more anchors may be configured to be deployed through a skin penetration point and into a subcutaneous region along an underside of a skin layer. The anchor device may further include a retainer base coupled to the first and second anchors. The retainer base may include a first channel, and the first channel may be configured to receive an external portion of a medical instrument occupying the skin penetration point. The anchor device may also include a cap that is releasably attachable with the retainer base so as to couple the medical instrument in a position between the cap and the retainer base. The cap may include a second channel, and optionally, a depth of the first channel is greater than a depth of the second channel.

In particular embodiments described herein, a medical anchoring system may include a medical instrument and an anchoring device. The medical instrument may be configured to occupy a skin penetration point while an external portion of the medical instrument resides external to the skin penetration point. The anchor device may include one or more anchors each having a longitudinal shaft portion and a tine disposed at a distal region of the longitudinal shaft portion. At least a portion of the one or more anchors may be configured to be deployed through a skin penetration point and into a subcutaneous region along an underside of a skin layer. The anchor device may also include a retainer base coupled to the first and second anchors. The retainer base may include a first channel, and the first channel may be configured to receive the external portion of the medical instrument when the medical instrument is occupying the skin penetration point. The anchor device may also include a cap that is releasably attachable with the retainer base so as to couple the external portion of the medical instrument in a position between the cap and the retainer base. Optionally, a depth of the first channel of the retainer base is greater than a height of the external portion of the medical instrument.

These and other embodiments may provide one or more of the following advantages. First, some embodiments of an anchor system can retain a medical instrument in a desired position relative to a skin penetration point without necessarily requiring sutures or skin adhesives. Second, in some embodiments, the anchor device may be adjusted between a folded configuration and a non-folded configuration so that the subcutaneous anchors are arranged side-by-side and extend in generally the same direction during both installation through and removal from the skin penetration point. In these circumstances, the subcutaneous anchors may be readily installed and removed from the skin penetration without the need for a separate external actuator or delivery device. Third, in some embodiments, the configuration of the medical device anchor system can simplify the process of coupling a medical instrument onto the anchor device. Fourth, in some embodiments the configuration of the medical device anchor system can reduce the likelihood of user errors related to improper coupling of the medical instrument to the anchor device. Fifth, in some embodiments the anchor devices include caps with universal designs that can be coupled with any one of different sizes of anchor device bases, thereby permitting a user to secure the cap and base combination to medical instruments of a range of sizes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A is a top perspective view of the anchor device of FIG. 1 with a cap of the anchor device fully separated from the base of the anchor device.

FIG. 2B is a top perspective view of the anchor device of FIG. 2A with the cap in a latched position on the base of the anchor device.

FIG. 3A is a bottom perspective view of the anchor device of FIG. 1 with the cap of the anchor device fully separated from the base of the anchor device.

FIG. 3B is a bottom perspective view of the anchor device of FIG. 3A with the cap in a latched position on the base of the anchor device.

FIG. 6 is a top perspective view of another anchor device embodiment with a cap of the anchor device fully separated from the base of the anchor device, in accordance with some embodiments.

FIGS. 7A and 7B are rear views of the anchor device of FIG. 6 with the cap in unlatched and latched positions respectively.

Like reference symbols in the various drawings indicate like elements.

DETAILED DESCRIPTION OF ILLUSTRATIVE EMBODIMENTS

Figure 1:
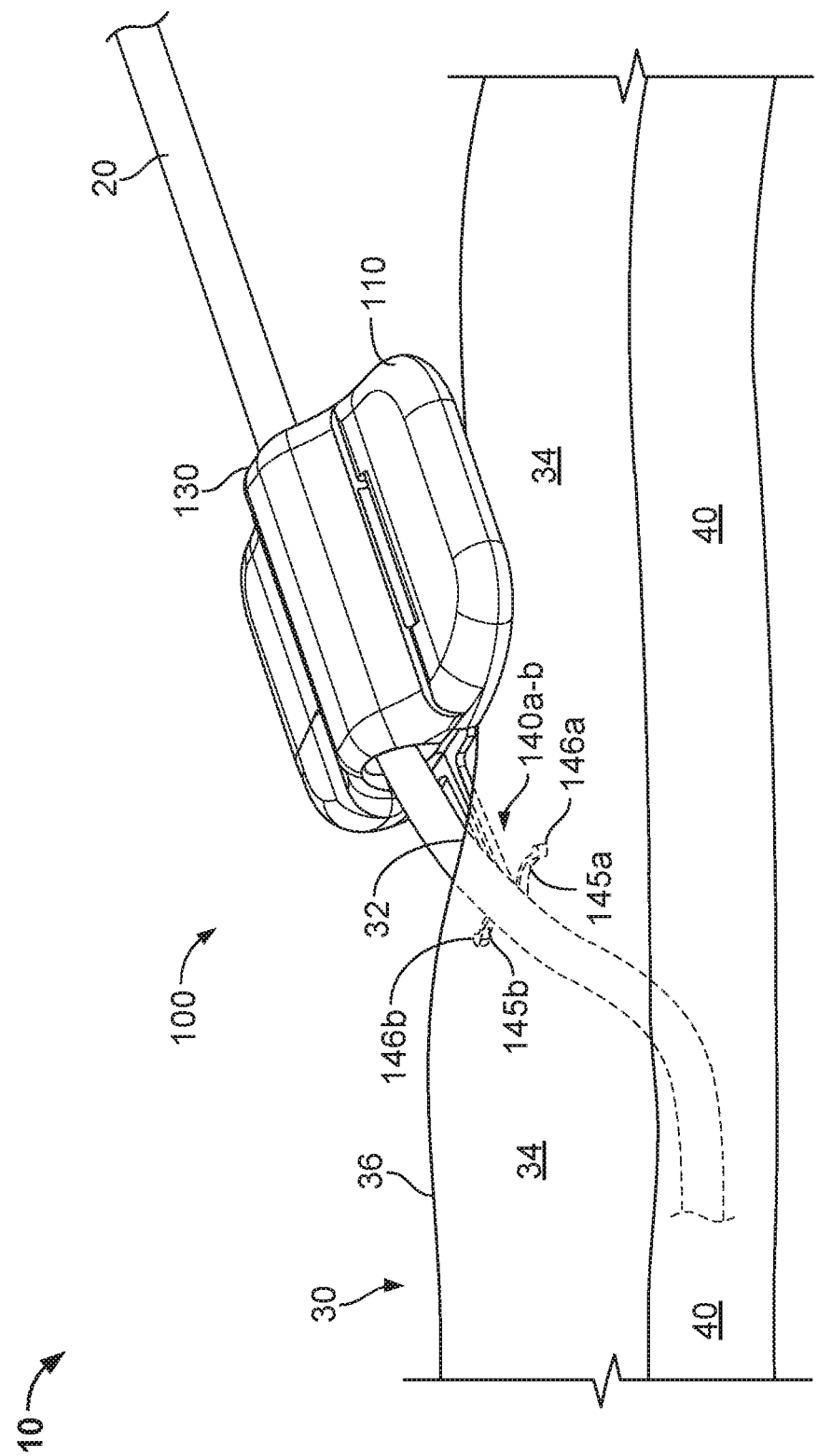
FIG. 1 is a perspective view of a medical instrument anchor system with a portion of the anchor device located in a subcutaneous region, in accordance with some embodiments.

Referring to FIG. 1, some embodiments of a medical device anchor system 10 include an anchor device 100 for releasably retaining a medical instrument 20 in an operative position relative to a portion of skin 30 (e.g., relative to a skin penetration point 32). In general, the example anchor device 100 provided herein includes a retainer base 110 and a cap 130. The base 110 can include one or more anchors 140a-b that extend distally from a distal end face of the base 110 for deployment in a subcutaneous layer 34. The anchors 140a-b can releasably couple the anchor device 100 to the skin penetration point 32. In some embodiments, the base 110 and the cap 130 are configured to grip an outer surface of the medical device 20 therebetween, so as to releasably couple the medical instrument 20 to the anchor device 100. In this manner, the medical device anchor system 10 can act as an intermediary member to retain the medical instrument 20 in a desired position with respect to the skin 30, without necessarily requiring sutures or adhesive tapes bonded to the skin. As described in more detail below, the cap 130 can be configured to readily and releasably couple with the base 110 in a simplified manner and, optionally, using a single hand of a user.

In the example implementation shown in FIG. 1, the medical instrument 20 is depicted as a catheter, such as a central venous catheter. Hereinafter the medical instrument 20 may alternatively be referred to as "catheter" 20 without limiting the medical instrument 20 to such an embodiment. In some implementations, the shaft of the catheter 20 may be inserted through a percutaneous opening formed in the skin (e.g., penetration point 32 defined by a small incision, a puncture, or the like), and may extend distally under the skin 30 (e.g., into a selected body vessel 40). The distal end of the catheter 20 may be positioned within the vessel 40 to provide vascular access for delivering medications, withdrawing fluids, or providing minimally invasive access into a patient. Although not shown in FIG. 1, a proximal portion of the catheter 20 may include a hub and/or multiple lumens that extend as isolated internal lumens along the proximal length of the catheter 20.

The anchors 140a-b can be permanently connected to, and extend distally from, the base 110. For example, the anchors 140a-b can be joined with the base 110 such that the anchors 140a-b extend distally from a distal-most face of the base 110. In some embodiments, the anchors 140a-b are embedded in the material of the base 110 using an insert overmolding manufacturing process. In alternative embodiments, the anchors 140a-b can be connected to the base 110 by a heat-staking process. Alternatively, other methods such as ultrasonic welding, RF welding, adhesive bonding and other suitable methods are used to connect the anchors 140a-b to the base 110.

Still referring to FIG. 1, at least a portion of each anchor 140a-b comprises a flexible material. In some embodiments, the anchors 140a-b may comprise a material that exhibits superelasticity. For example, in some embodiments at least a portion of the anchors 140a-b (including the tines 145a-b) may be formed from a length of nitinol wire, or from a sheet of nitinol material. Alternatively, the anchors 140a-b may comprise another metal material that can provide a selected degree of flexibility, such as stainless steel (e.g., 304 stainless, 316 stainless, custom 465 stainless, and the like), spring steel, titanium, MP35N, and other cobalt alloys, or the like. In another alternative, the anchors 140a-b may be formed from a resilient polymer material. In some embodiments, the anchors 140a-b can be formed from other materials that allow the tines 145a-b to be flexed and resiliently return to a selected arrangement.

Still referring to FIG. 1, the anchors 140a-b include subcutaneous tines 145a-b that, after insertion, reside in a subcutaneous region 34 (e.g., a region immediately under the skin 30 that may often comprise a fatty tissue layer) so as to secure the position of the anchor device 100—and the catheter 20 retained thereto—relative to the skin penetration point 32. In the embodiment depicted, each of the anchors 140a-b may be designed such that the tines 145a-b have an unstressed orientation wherein the tines 145a-b have a convex curvature. The convex curvature shape of the tines 145a-b may permit the tines 145a-b to abut against the underside of the dermal layers in a manner that reduces the likelihood of the tine tips 146a-b puncturing the underside of the dermal layers. Preferably, the tine tips 146a-b are rounded bulbs or otherwise non-sharp so as to further protect the underside of the dermal layers. In alternative embodiments, the tines 145a-b may have a generally straight shape that extends substantially perpendicular to the longitudinal shaft portions of the anchors 140a-b to the rounded tips 146a-b.

As described in more detail below in connection with FIGS. 5A-5C, the anchor device 100 can be advantageously installed through the skin penetration point 32 in accordance with a technique that reduces or eliminates the need to significantly stress (significant flexing of) the subcutaneous anchors tines 145a-b of the anchors 140a-b. When the tines 145a-b are deployed in the subcutaneous region 34, the anchor device 100 can be secured to the patient while the base 110 remains entirely external to the skin (without the base 110 penetrating through the dermal layers of the patient), and without necessarily requiring sutures or adhesive tapes bonded to the skin 30.

Referring to FIGS. 2A-B and 3A-B, the example anchor device 100 is depicted in top and bottom perspective views respectively. FIGS. 2A and 3A depict the anchor device 100 in an exploded configuration from top and bottom views respectively. FIGS. 2B and 3B depict the anchor device 100 in a latched configuration from top and bottom views respectively.

Referring particularly to FIGS. 2A and 3A, the base 110 and the cap 130 of the example anchor device 100 are depicted in an exploded or fully decoupled configuration. That is, FIGS. 2A and 3A illustrate that in some embodiments the base 110 and the cap 130 can be readily separable parts. However, in other embodiments, the base 110 and the cap 130 are not readily separable. For example, in some embodiments, the base 110 and the cap 130 can be pivotably connected by a living hinge, a hinge with a pin, or other mechanical joinery methods. In other embodiments, the base 110 and the cap 130 can be coupled together using a variety of other kinds of mechanical features such as spring clips, compression fits, over-center linkages, clamps, and the like.

Referring again to FIGS. 2A-B and 3A-B collectively, in some embodiments the base 110 and the cap 130 comprise one or more biocompatible polymer materials (e.g., polypropylene, polystyrene, acrylonitrile butadiene styrene (ABS), polycarbonate, PVC, silicone, or the like). In some embodiments, the base 110 and the cap 130 are made from substantially the same type of material. In alternative embodiments, the base 110 and the cap 130 are made from dissimilar types of materials. In some embodiments, the base 110 and/or the cap individually comprise a single type of material. In alternative embodiments, the base 110 and/or the cap individually comprise a combination of two or more types of materials. For example, in the embodiment depicted in FIGS. 2A and 3A, device engagement portions 116 and 138 can comprise a soft durometer material such as an elastomeric polymer while other portions of the base 110 and the cap 130 can comprise a less flexible polymer material such as polypropylene, PVC, polystyrene, or the like. In other embodiments, just the base 110 includes device engagement portion 116 comprising the soft durometer material, while the cap 130 solely comprises the less flexible polymer. In another example, an elastically flexible folding region 150 of the base 110 (refer to FIGS. 2A-B and 3A-B) can comprise an elastically flexible silicone material, while other portions of the base 110 can comprise a less flexible polymer material such as polypropylene, PVC, polystyrene, or the like. However, in alternative embodiments the folding region 150 can comprise polypropylene, PVC, polystyrene, or other similar materials that are consistent with the other portions of the base 110.

In some embodiments, surfaces of tab portions on the base 110 and/or the cap 130 can comprise a material that is well-suited for convenient and ergonomic physical contact and manipulation by human fingers. For example, the gripping regions 111 and 115 shown in FIGS. 2A, 2B, 4A, and 4B can comprise a soft elastomer such as a thermoplastic elastomer, silicone, or the like. The gripping regions 111 and 115 can thereby be conveniently soft and/or tacky to assist a user with manipulation of the anchor device 100. In some cases, the gripping regions 111 and 115 can be textured using surface features such as knurling, stippling, dimpling, or ridges. The gripping regions 111 and 115 can have a contrasting color in comparison to other portions of the anchor device 100. Such color differences can signal to a user that the gripping regions 111 and 115 are intended to provide locations for the user to grip the anchor device 100.

At least some portions of the base 110 and/or the cap 130 can be formed using a molding process. In some cases, some portions of the base 110 and/or the cap 130 can be manufactured as separate parts that are later joined to other portions of the base 110 and/or the cap 130. For example, the base 110 can be over-molded around the anchors 140a-b (e.g., especially in those embodiments in which the anchors 140a-b comprise a metallic material). In alternative embodiments, other initially separate portions of the base 110 and/or the cap 130 can be subsequently over-molded, insert molded, glued, heat-staked, welded, press-fit, or otherwise attached to other portions of the base 110 and/or the cap 130. For example, the device engagement portions 116 and 138 and/or the gripping regions 111 and 115 comprising the soft and/or tacky material(s) can be over-molded, insert molded, glued, heat-staked, welded, press-fit, or otherwise attached to other portions of the base 110 and/or the cap 130.

Still referring to FIGS. 2A-B and 3A-B, the base 110 in this embodiment includes the anchors 140a-b, a base grip tab 112, a base twist tab 114, a device engagement portion 116, a fold axis 118, and a slot 120. Description of the anchors 140a-b is provided primarily in reference to FIGS. 1 and 5A-5E, and descriptions of the device engagement portion 116 and the fold axis 118 defined by the flexible folding region 150 are provided primarily in reference to FIGS. 5A-5E.

In some embodiments, the base grip tab 112 is a generally flat surface of the base 110 that can provide a convenient location for a user to ergonomically grip and manipulate the base 110. For example, in some cases the user may desire to stabilize the base 110 when the cap 130 is being latched or unlatched with the base 110 (as described further in reference to FIGS. 4A and 4B). In such cases, the base grip tab 112 can provide a convenient user gripping location to stabilize the base 110. Further, while folding the base 110 for insertion or removal from a skin penetration point 32 (refer to FIG. 5A), the base grip tab 112 can provide a suitable region by which the user can grip and manipulate the base 110. That is, the user can grip the base grip tab 112 to induce folding of the base 110, and to maintain the base 110 in the folded configuration. In another example, the base grip tab 112 can be a convenient user gripping location while raising the anchor device 100 to clean the patient's skin under the anchor device 100. In some embodiments, at least a portion of the surface of the base grip tab 112 is configured for convenient user gripping by comprising a soft durometer elastomeric material.

In some embodiments, the base twist tab 114 is another generally flat surface located on the base 110. The base twist tab 114 can provide another convenient location for a user to ergonomically grip and manipulate the base 110. As described above in regard to the base grip tab 112, the base twist tab 114 can be a convenient user gripping location for folding the base 110. In another example, the base twist tab 114 can be conveniently used to induce the latching and unlatching of the cap 130 with the base 110. That is, as further described in reference to FIGS. 4A and 4B, when a user's finger or thumb is placed on the base twist tab 114, and the user's opposing finger or thumb is placed on the cap 130 (e.g., on a cap twist tab 134), a twisting motion of the user's hand or wrist can induce the latching or unlatching of the anchor device 100. In some embodiments, at least a portion of the surface of the base twist tab 114 is configured for convenient user gripping by comprising a soft durometer elastomeric material.

As illustrated in FIGS. 2A-B, both the base grip tab 112 and the base twist tab 114 remain exposed even when the cap 130 is fully secured to the base 110. Also, in this embodiment, the outer profile shape of the base 110 is different from the outer profile shape of the cap 130. As such, the cap 130 can have a maximum length or maximum width (or both) that is less than the corresponding maximum length or width of the base 110.

In some embodiments, the base 110 further includes a slot 120 feature. The slot 120 can be configured to releasably engage with a portion of the cap 130 (e.g., a projection 132) in a cooperative fashion. For example, in some embodiments the slot 120 is a cut-out portion of the base 110 that is shaped to receive the complementary shaped projection 132 located on the cap 130. (In alternative embodiments, the base 110 can include the projection and the cap 130 can include the slot.) As shown in FIGS. 2A and 3A, the slot 120 extends fully through the base 100. Alternatively, the slot 120 may be formed as a channel with a bottom portion and sidewalls rather than being a slot 120 with no bottom. As described in more detail below, the relationship between the slot 120 and the projection 132 provides a pivotable and releasable connection between the base 110 and the cap 130. Other alternative types of mechanisms can be used to provide cooperative engagement between the base 110 and the cap 130. For example, other types of hinges, clamps, bands, pins, and the like can be used to provide the desired type of mechanical engagement between the base 110 and the cap 130.

The shapes of the slot 120 and the projection 132 can complement each other to enable a desired range of motion of the cap 130 in relation to the base 110 while the projection 132 in coupled with the slot 120. For example, in some embodiments the projection 132 has a flared configuration (e.g., extends outwardly at a particular radius) and the slot 120 has a complementary radius. The radiused configurations of the projection 132 and the slot 120 can thereby guide a pivotable range of motion between the cap 130 and the base 110. In such configurations, the cooperation between the slot 120 and the projection 132 provides a type of hinge joint to enable the cap 130 to pivot in relation to the base 110.

In some embodiments, the shapes of the slot 120 and the projection 132 can further complement each other so as to enable the cap 130 and the base 110 to be fully separable from each other. For example, in some embodiments the projection 132 can be separated from the slot 120 when the cap 130 is pivoted to a particular orientation in relation to the base 110 (e.g., an orientation wherein the cap 130 and the base 110 are approximately at a 90 degree angle to each other). With the cap 130 orientated in the particular orientation in relation to the base 110, the cap 130 can then be lifted off from the base 110 and fully separated from the base 110. To re-engage the cap 130 with the base 110, the cap 130 can be positioned in the particular orientation and the projection 132 can be inserted into the slot 120. Then, with the projection 132 within the slot 120, the cap 130 can be pivoted in relation to the base 110 (refer to FIGS. 4A and 4B).

In some embodiments, the cap 130 and the base 110 can also include complementary features that enable the cap 130 to be latched to the base 110 (e.g., to thereby couple a medical device 20 to the anchor device 100). In some embodiments, the cap 130 can be releasably snap-locked onto the base 110. For example, in some embodiments the base 110 includes a projection 122 configured to act as a tongue or tenon (best seen in FIG. 3A), and the cap 130 includes a complementary groove 135 and a lip 136. When the projection 132 of the cap 130 is engaged with the slot 120 of the base 110, the cap 130 can be latched to the base 110 by positioning the projection 122 within the groove 135, such that the lip 136 is located on the underside of the projection 122 (best seen in FIG. 3B).

Figure 4A:
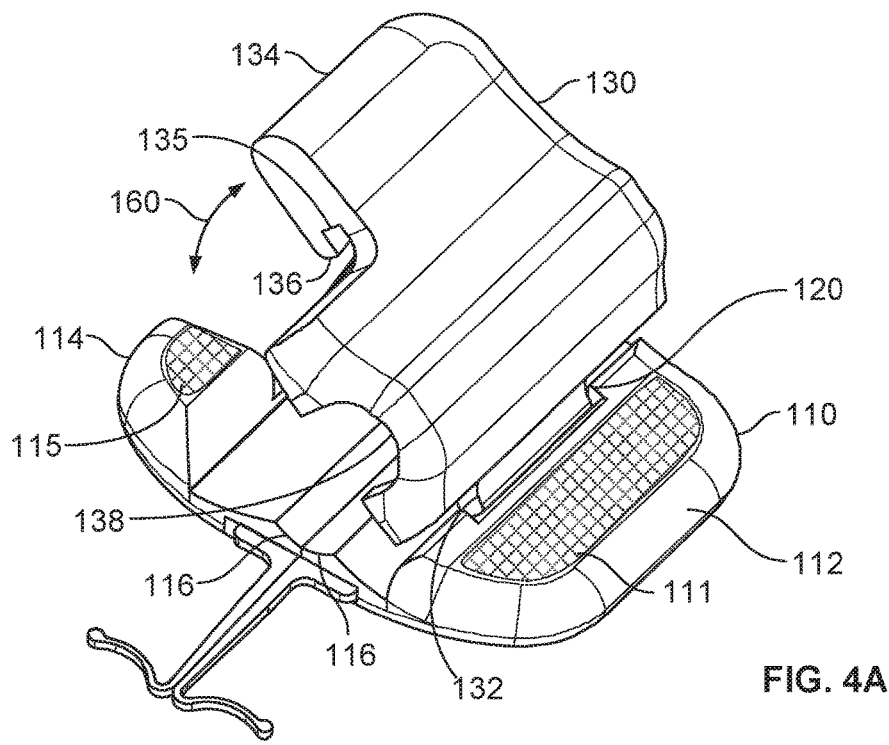
FIGS. 4A and 4B are perspective views of the anchor device of FIG. 1 with the cap in unlatched and latched positions respectively.
Figure 4B:
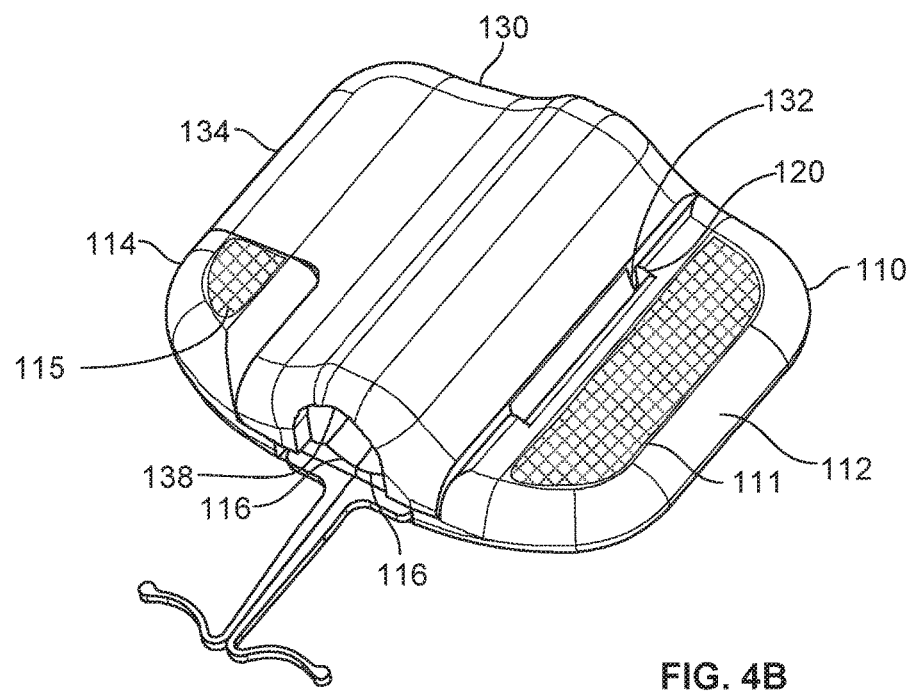

Referring to FIGS. 4A and 4B, the pivotable relationship between the cap 130 and the base 110, and the latching of the cap 130 to the base 110 is depicted. As described above, the projection 132 can be mated with the slot 120 to enable the pivoting motion of the cap 130 is relation to the base 110. In that manner, the projection 132 and the slot 120 can function together like a hinge to enable the cap 130 to be pivoted in relation to the base 110 as depicted by arrow 160. The cap 130 can be latched to the base 110 when the cap 130 is pivoted down onto the base 110 such that the projection 122 becomes engaged within the groove 135, as described further below. In particular embodiments (not shown), the cap 130 can be fixedly coupled in a pivotable arrangement with the base 110, rather than being separable from the base 110 as shown. For example, the cap 130 can be molded as a unitary part with the base 110, whereby a living hinge is created between the cap 130 and the base 110 to create a fixed pivotable relationship between them. In another example, a portion of the cap 130 can be fixedly press-fit onto the base 110 to create a fixedly pivotable coupling between them. In further examples, rather than press-fitting, the fixedly pivotable coupling between the cap 130 and the base 110 can be created by using an adhesive, heat-staking, ultra-sonic welding, over-molding, and the like.

In this embodiment, the cap 130 and the base 110 can be described as having at least three configurations in relation to each other. A first configuration of the cap 130 and the base 110 is a fully decoupled configuration. That is, the cap 130 can be fully separated from the base 110 as shown in FIGS. 2A, 3A, and 5A-5D. This configuration can provide user convenience at times, such as when the base 110 is to be folded for insertion into or removal from a skin penetration point 32 (refer to FIGS. 5A and 5B).

A second configuration of the cap 130 and the base 110 is a coupled-but-unlatched configuration. This second configuration is depicted in FIG. 4A. The cap 130 is pivotably coupled with the base 110 because the projection 132 is cooperatively engaged with the slot 120. In this configuration, while the cap 130 is coupled to the base 110, the cap 130 is not latched with the base 110. As such, the cap 130 can be moved within a range of motion in relation to the base 110. For example, in some embodiments the cap 130 can be pivoted in relation to the base 110 as depicted by arrow 160. This configuration can provide user convenience at times, such as when the user desires to couple or uncouple a medical device 20 from the anchor device 100.

A third configuration of the cap 130 and the base 110 is a latched configuration. This third configuration is depicted in FIGS. 1, 2B, 3B, 4B, and 5E. In the latched configuration, the cap 130 is fully coupled to the base 110. That is, the projection 132 is engaged with the slot 120, and the projection 122 is engaged within the groove 135. In this configuration, a medical device 20 can be releasably coupled to the anchor device 100. In other words, in the latched configuration the base device engagement portion 116 and a cap device engagement portion 138 can exert a light compressive force on the medical device 20 to thereby couple the medical device 20 to the anchor device 100 using a friction fit. In some embodiments, at least a portion of the surfaces of the device engagement portions 116 and 138 are lined with a soft durometer elastomer that provides a compliant gripping interface between the anchor device 100 and the medical device 20. In particular embodiments, the device engagement portion(s) define shapes that are more complementary with the shape of the medical device that will be engaged with the anchor device 100. For example, (as described further in reference to FIGS. 6 and 7A-7B), the engagement portions can define a deeper groove that provides a more robust engagement with the outer circumferential surface of a catheter while also reducing the likelihood of "pinching" the outer wall of the catheter.

The latched configuration also beneficially serves to maintain the base 110 in a substantially flat or unfolded configuration during use of the anchor device 100. That is true because the cap 130 acts as a stabilizing link that is orthogonal the fold axis 118. The cap 130 thereby inhibits the base 110 from folding. This feature can help to maintain the anchor device 100 in a proper operative position in relation to the skin penetration point 32 during use.

As depicted in FIGS. 4A and 4B, the cap 130 can be releasably attached to the base 110 in a simplified manner. In some embodiments, to latch the cap 130 to the base 110, the cap 130 is first pivoted about the hinge-like axis created by the cooperation of the projection 132 and the slot 120, such that the cap 130 pivots down onto the base 110. As the cap 130 is pivoted onto the base 110, the lip 136 of the cap 130 will come into contact with the projection 122 of the base 110. In some embodiments, a mechanical interference exists between the lip 136 of the cap 130 and the projection 122 of the base 110 as the cap 130 is pivoted onto the base 110. In some embodiments, in order for the cap 130 to latch to the base 110 (such that the projection 122 becomes engaged within the groove 136), the lip 136 passes beyond the interference presented by the projection 122 so as to provide a snap fit engagement.

In some embodiments, to enable the latching of the cap 130 to the base 110, at least portions of the projection 122 or the lip 136 (or both the projection 122 and the lip 136) are comprised of a flexible material that is conveniently deflectable by user manipulation of the anchor device 100. For example, in some embodiments the lip 136 comprises a flexible elastomer material that can be deflected to enable the lip 136 to pass over and beyond the projection 122, such that the projection 122 becomes engaged within the groove 135. In some embodiments, the projection 122 can comprise a flexible material for the same purpose. In some embodiments, other portions of the cap 130 or the base 110 can be flexible to similarly enable the user to overcome the mechanical inference between the lip 136 and the projection 122, and to thereby latch the cap 130 to the base 110.

In some embodiments, the user can provide the force to overcome the mechanical inference between the lip 136 and the projection 122 by applying a pinching force to the cap 130 and the base 110 simultaneously. For example, in some cases the user may place a thumb on the cap twist tab 134 and an index finger below the base twist tab 114, and then pinch or twist the cap 130 and the base 110 towards each other. In that fashion, a single hand of the user can apply the force needed to overcome the mechanical inference between the lip 136 and the projection 122, to thereby latch the cap 130 to the base 110.

In some embodiments, the user can unlatch the cap 130 from the base 110 using a similar technique. For example, the user may place a thumb under the cap twist tab 134 and an index finger on the base twist tab 114, and then twist or otherwise separate the cap 130 away from the base 110. In that fashion, the user can apply the force needed to overcome the mechanical inference between the lip 136 and the projection 122, to thereby unlatch the cap 130 from the base 110.

The aforementioned mechanisms provided by the anchor device 10 for latching and unlatching the cap 130 from the base 110 can provide beneficial features to the user. In some embodiments, the techniques used for the latching and unlatching of the cap 130 and the base 110 can be conveniently performed using just one hand (e.g., a thumb and opposing index finger as described above). In some embodiments, the mechanisms used to latch the cap 130 to the base 110 can provide readily discernible snap-lock latching feedback. That is, in some embodiments the passage of the projection 122 beyond the lip 136 and into the groove 135 can provide audible and/or tactile sensory feedback to the user, by which the user can readily discern that the cap 130 has properly latched onto the base 110. Such a snap-lock feature may reduce the likelihood of partial or improper latching of the cap 130 and the base 110, which can in turn enhance the efficacy of the medical device anchor system 10, as well as user safety, confidence, and convenience.

Referring to FIGS. 5A-5E, some implementations of a process for using the medical device anchor system 10 can provide a convenient and flexible securement of the medical instrument 20 to the skin penetration point 32. In such implementations, the anchor device 100 can deploy the anchors 140a-b through the same skin penetration point 32 as the medical instrument 20, and furthermore, the anchor device 100 can then releasably retain an external portion of the medical instrument 20 during the duration of a medical use. In the illustrated example, the medical instrument is a central venous catheter 20 that is inserted percutaneously through a skin penetration point 32 surgically formed in the skin 30, and into a vessel to provide vascular access for delivering medications or minimally invasive devices into a patient.

Figure 5A:
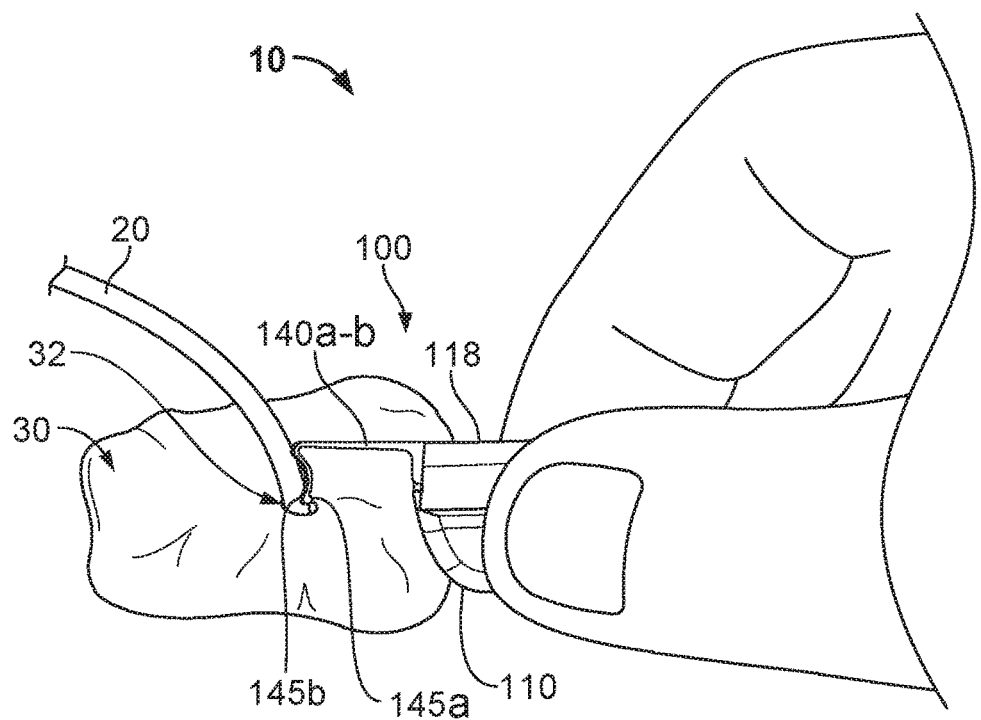
FIGS. 5A-5E are perspective views depicting an example process for deploying a medical instrument anchor system, including the anchor device of FIG. 1, and for securing the position of the medical instrument at a skin penetration point.
Figure 5B:
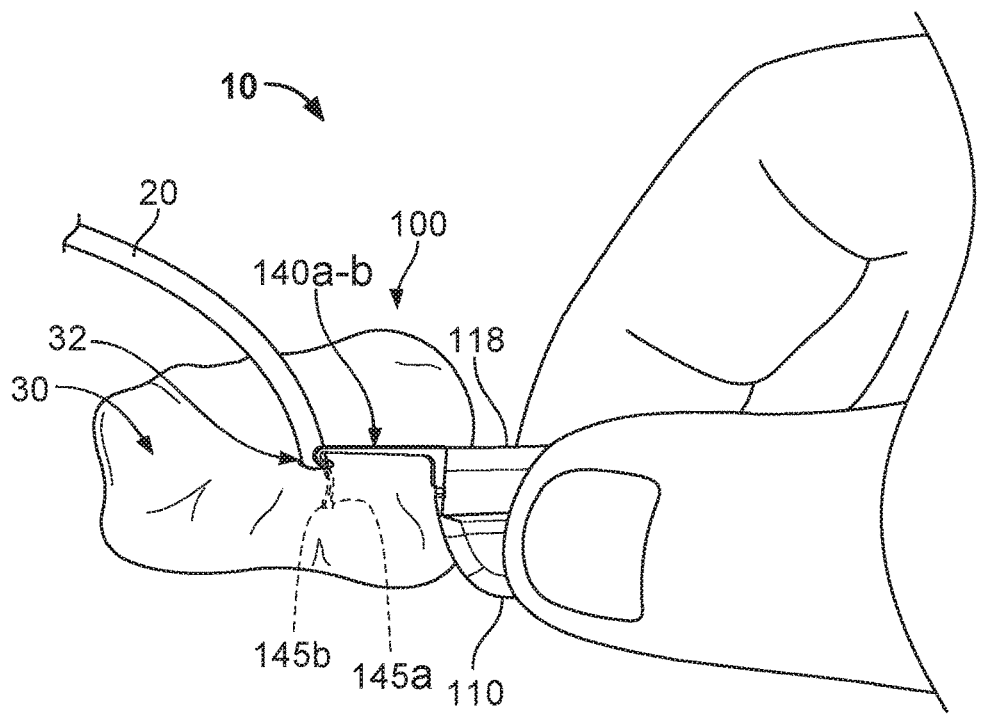

As shown in FIGS. 5A and 5B, after placement of the catheter 20 through the penetration point 32 of the skin 30, the anchor device 100 can be installed. During the installation of the anchor device 100, the cap 130 is unlatched from the base 110. In some cases, the cap 130 is fully decoupled from the base. The user can grasp the anchor device 100 and fold the anchor device 100 along fold axis 118 such that the tines 145a-b are in a generally side-by-side arrangement. The user can then move the anchor device 100 near the penetration point 32 such that the free ends of the tines 145a-b are contemporaneously inserted through the penetration point 32 while the tines 145a-b are in the generally side-by-side arrangement. The user can apply an insertion force until the convexly curved body portions of the subcutaneous tines 145a-b are positioned below the surface of the skin 30 as shown in FIG. 5B (while the remainder of the anchor device 100 resides external to the skin 30).

As the tines 145a-b of the anchor device 100 are inserted through the penetration point 32, the tines 145a-b may be maintained in the generally side-by-side arrangement while passing through the penetration point 32 so as to reduce the likelihood of trauma to the surrounding skin tissue 30. As the tines 145a-b are collectively advanced through the penetration point 32, the free ends of the tines 145a-b are moved beneath the dermal skin layers of the skin 30.

Figure 5C:
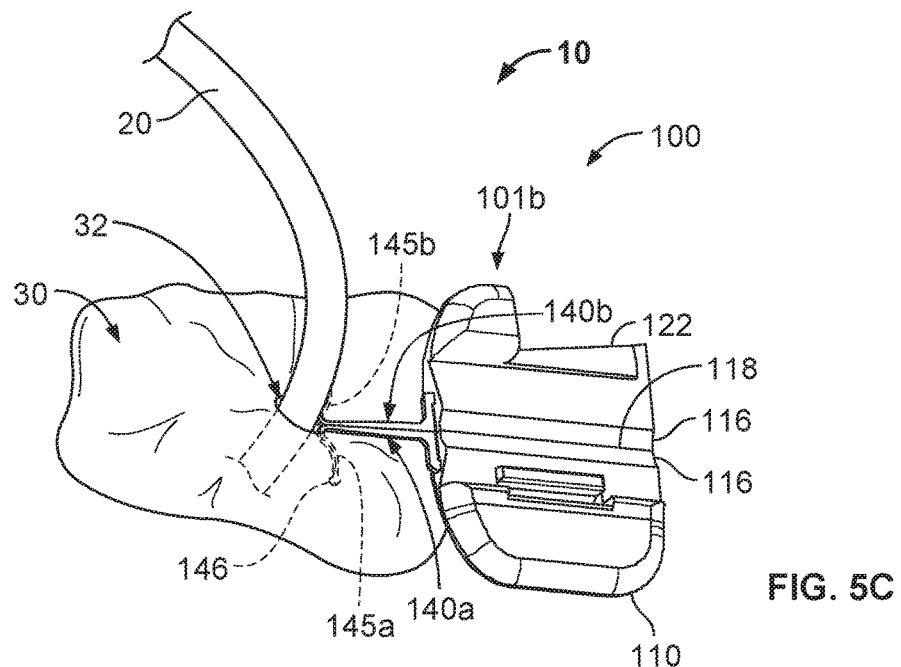

When the tines 145a-b reach the subcutaneous region, the base 110 can adjusted to the unfolded condition so that the tines 145a-b are shifted relative to one another, resulting in the tines 145a-b extending outwardly away from one another (as depicted in FIG. 5C). During that process of unfolding the base 110, each tine 145a-b may optionally retain its original shape (e.g., the first shape or the steady-state shape). Thus, the anchor device 100 can be installed in accordance with a technique that reduces or eliminates the need to significantly stress (e.g., significant flexing of) the subcutaneous anchors tines 145a-b during the passage through the skin penetration point 32.

Figure 5D:
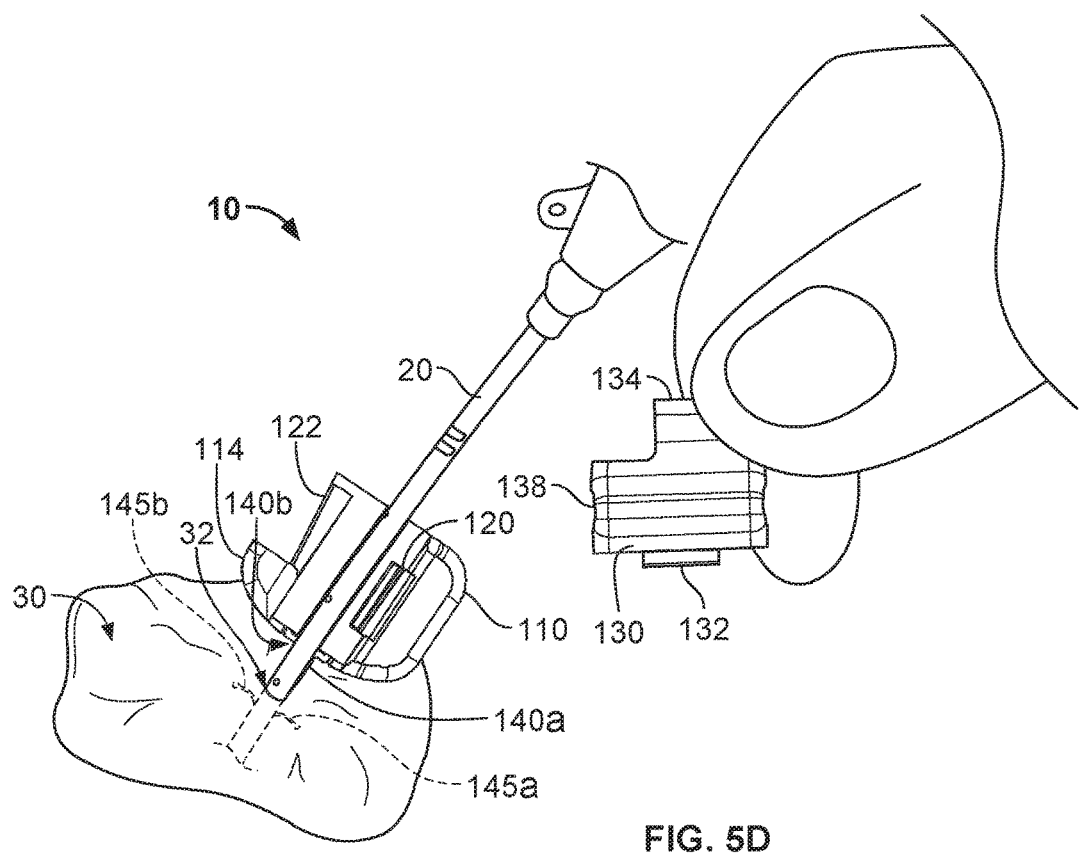

Referring now to FIGS. 5C-5D, the medical device anchor system 10 can secure the medical instrument 20 relative to the skin penetration point 32. With the anchor device 100 positioned such that subcutaneous anchors tines 145a-b are in their deployed configuration (FIG. 5D), the previously inserted catheter 20 can be releasably secured to the anchor device 100. At this juncture of the medical device anchor system 10 deployment process, the cap 130 can be coupled to the base 110, and then latched to the base 110. In that manner, the catheter 20 can become coupled to the anchor device 100.

To couple the cap 130 to the base 110, the user can manipulate the cap 130 to position the projection 132 in the slot 120. With the projection 132 cooperatively engaged with the slot 120, the user can pivot the cap 130 down onto the base 110. At this point the catheter 20 will be captured between the device engagement portions 116 and 138. To latch the cap 130 with the base 110, the user can apply a simple pinching force, for example, on the base twist tab 114 and the cap twist tab 134 as described above. When a sufficient force is so applied, the cap 130 will snap into a latched position on the base 110.

Figure 5E:
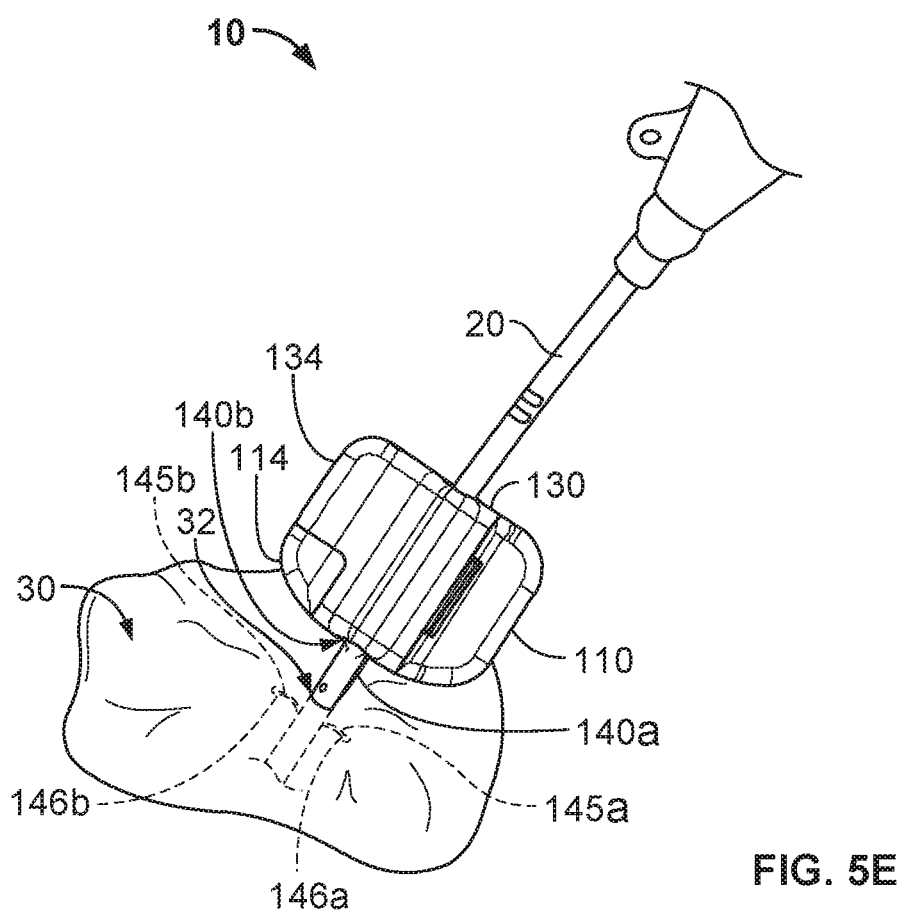

Referring now to FIG. 5E, the catheter 20 is releasably coupled with the anchor device 100 so that the catheter 20 is anchored to the skin penetration point 32. The medical device anchor system 10 releasably retains the catheter 20 in an operative position relative to a portion of skin 30 (e.g., the skin penetration point 32). The medical instrument 20 is mechanically coupled to the anchor device 100 as described above. The anchor device 100, in turn, is anchored to the portion of skin 30 via the anchors 140a-b that are deployed into the subcutaneous region. In such embodiments, the medical device anchor system 10 can be secured to the patient without necessarily requiring sutures or adhesive tapes bonded to the skin 30. The catheter 20 penetrates a skin penetration point 32 and distally extends into the subcutaneous layers. Such a configuration provides a compact medical device anchor system 10 that is convenient to install and maintain.

Removal of the medical device anchor system 10 can be performed by generally reversing the sequence of tasks described above. For example, the cap 130 can be unlatched from the base 130. In some embodiments, to unlatch the cap 130 from the base 110, the user can apply a twisting force to the base twist tab 114 in relation to the cap twist tab 134 as described above. When sufficient force is applied, the cap 130 will unlatch from the base 110 as described above. The cap 130 can then be pivoted in relation to the base 110. When the cap 130 has been pivoted to the decoupling position, the cap 130 can be fully decoupled from the base 110. The base 110 can be folded and the tines 145a-b can be removed from the subcutaneous tissue through the skin penetration point 32. Optionally, the base 110 can be folded without fully decoupling the cap 130 from the base 110. If required, the catheter 20 can also be removed from the patient by withdrawing the catheter 20 out through the skin penetration point 32.

Referring now to FIGS. 6 and 7A-7B, in another example embodiment, an anchor device 200 includes a base 210 and a cap 230 that releasably attaches to the base 210 in a pivoting movement. FIG. 6 is an exploded perspective view of the anchor device 200, and FIGS. 7A and 7B are rear views (from view A-A of FIG. 6) showing the anchor device 200 in unlatched and latched configurations respectively. In general, anchor device 200 is similar to the previously described anchor device 100 from FIGS. 1-5E. In this embodiment, however, the anchor device 200 has device engagement portions 216 and 238 that are different than the device engagement portions 116 and 138 of anchor device 100. In particular, the device engagement portion 216 of anchor device 200 defines a deeper receiving channel that is suitable for releasably seating a catheter 20 or other medical instrument therein (refer to FIG. 7B). In particular circumstances, the receiving channel 217 having a deeper aspect along the base 210 permits a user to conveniently retain the catheter 20 in the channel 20 (e.g., due to a frictional engagement with the portions 216 and 238) before the cap 230 is fully secured to the base 210. Furthermore, the device engagement portion 216 provides the receiving channel 217 having a deeper aspect along the base 210 while the other engagement portion 238 (along the cap 230) has a smaller profile to engage a smaller region of the catheter 20, thereby reducing the likelihood of "pinching" an outer wall of the catheter 20 during the process of securing the cap 230 to the base 210.

Similar to the previously described device engagement portions 116 and 138 (previously described in connection with FIGS. 2A-B and 3A-B), the engagement portions 216 and 238 in this embodiment can comprise a tacky and/or soft durometer elastomer such as a thermoplastic elastomer, silicone, or the like—or combinations of such materials. Such materials can enable the engagement portions 216 and 238 to be flexible and compliant, thereby conforming to and frictionally gripping the outer surfaces of the catheter 20 or other medical instrument. The device engagement portions 216 and 238 can be over-molded, insert molded, glued, heat-staked, welded, press-fit, or otherwise attached to other portions of the base 210 and the cap 230. In some embodiments, the device engagement portions 216 and/or 238 can be removable from the base 210 and the cap 230 to enable the engagement portions 216 and/or 238 to be interchanged with other engagement portions that define different shapes. Such a feature can be used to enable an anchor device 200 to be coupled with various types of medical instruments that have varying shapes or sizes. Similar to previously described embodiments (e.g., as described in connection with FIGS. 4A-4B, the base 210 further includes a slot (not shown in FIGS. 7A-B) formed therein, which is configured to releasably engage with a portion of the cap 230 in a cooperative fashion. For example, in some embodiments the slot is a cut-out portion of the base 210 that is shaped to receive the complementary shaped projection (similar to projection 132 in FIGS. 4A-4B) located on the cap 230 so as to provide the claimed releasable securement via a pivoting motion. (In alternative embodiments, the base 210 can include the projection and the cap 230 can include the slot.)

Referring to FIGS. 7A-B, the device engagement portions 216 and 238 define channels 217 and 239 that are configured for engagement with the catheter 20 or another medical instrument. The engagement portion 216 defines the receiving channel 217 with a depth of $h_b$. The depth $h_b$ of the channel 217 may be greater than 50% of the outer diameter of the catheter 20, greater than about 70% of the outer diameter of the catheter 20, and is greater than the outer diameter of the catheter 20 in this illustrative example shown in FIGS. 7A-B. In such circumstances, the channel 217 is so dimensioned as to permit a user to lightly press the catheter 20 into the channel 217 so that it is temporarily retained therein (e.g., due to a frictional engagement with the engagement portion 216) during the process of securing the cap 230 to the base 210.

As shown in FIG. 7B, the engagement portion 238 defines a channel 239 with a depth of $h_c$. In general, the depth $h_b$ is substantially greater than the depth $h_c$. Also, in this particular embodiment, the channel 239 of the engagement portion 238 has a width that is small enough to fit into an upper mouth of the channel 217. Accordingly, when the cap 230 is secured to the base 210, the channel 239 of the engagement portion 238 can be moved toward the upper mouth of the catheter receiving channel 217 so that the channel 239 engages a smaller upper region of the catheter 20. In doing so, the engagement portion 238 of the cap device 230 firmly retains the catheter 20 from unseating out of the catheter receiving channel 217, yet the relationship between catheter receiving channel 217 and the channel 239 reduces the likelihood of "pinching" an outer wall of the catheter 20 during the process of securing the cap 230 to the base 210.

Figure 8A:
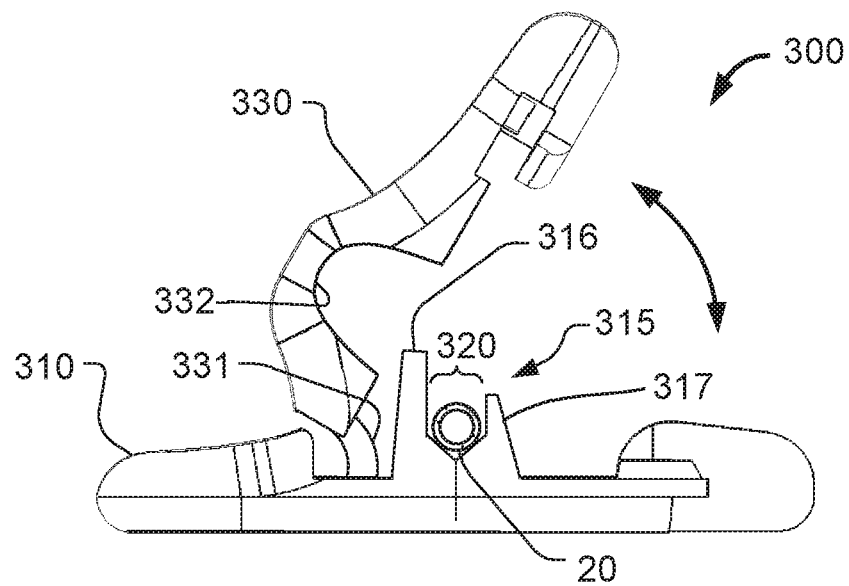
FIGS. 8A and 8B are rear views of an anchor device with an example universal cap in unlatched and latched positions respectively, in accordance with some embodiments.
Figure 8B:
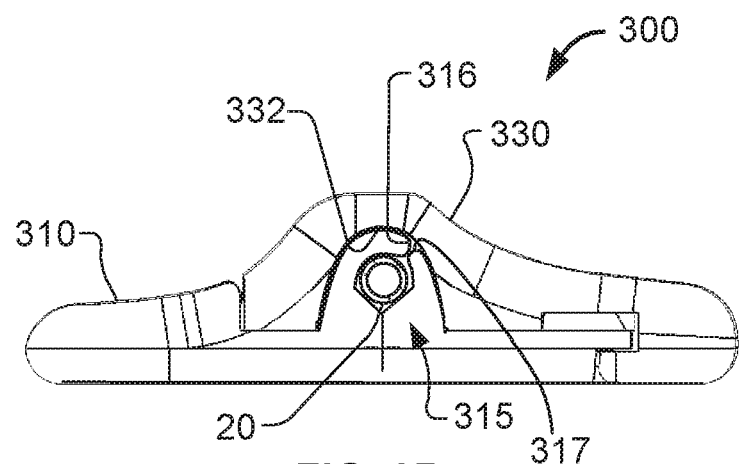

Referring to FIGS. 8A-8B, some embodiments of an anchor device 300 can include a cap 330 that is configured to match with any of a variety of differently sized bases 310, thereby providing a universal cap structure. As shown in FIGS. 8A-B, the cap 330 is illustrated in unlatched and latched configurations in relation to a base 310 selected from a set of differently sized bases (e.g., each including a differently sized channel 320 so as to receive different sizes of catheters or other medical instruments). The base 310 includes a device engagement portion 315 with a catheter receiving channel 320 defined by projections 316 and 317. The projections 316 and 317 are dissimilar in height as described further below. Device engagement portion 315 of the base can comprise a tacky and/or soft durometer elastomer such as a thermoplastic elastomer, silicone, or the like—or combinations of such materials. Such materials can enable the engagement portion 315 to be flexible and compliant, thereby conforming to and frictionally gripping the outer surfaces of the catheter 20, or other medical instrument. In some embodiments, the flexibility of the engagement portion 315 can also be used advantageously to couple with catheters of various sizes.

As previously described, the cap 330 can be releasably secured to any of a set of differently sized bases, which are configured to couple with a range of different sizes of medical instruments, such as the catheter 20 in this example. For example, in some cases a particular cap 330 embodiment can be used in combination with any of a set of differently sized bases 310 for coupling with a range of catheters covering about four French (Fr) sizes (e.g., from about 3 to 6 Fr, from about 4 to 7 Fr, from about 5 to 8 Fr, and so on). In some embodiments, the cap 330 can be used to couple with a greater range of catheter sizes covering about five (5), six (6), seven (7), eight (8), nine (9), ten (10), or a larger range, of Fr sizes. Similar to previously described embodiments (e.g., as described in connection with FIGS. 4A-4B, the base 310 further includes a slot (not shown in FIGS. 8A-B) formed therein, which is configured to releasably engage with a portion of the cap 330 (e.g., a projection 331) in a cooperative fashion. For example, in some embodiments the slot is a cut-out portion of the base 310 that is shaped to receive the complementary shaped projection 331 located on the cap 330 so as to provide the claimed releasable securement via a pivoting motion. (In alternative embodiments, the base 310 can include the projection and the cap 330 can include the slot.)

In some cases, the base 310 is configured to couple with a specific size of medical instrument (e.g., a 6 Fr. catheter, or the like). In other words, in some cases a specifically sized base 310 is used for each different size of medical instrument (while the cap coupled with the base can be a universal cap design that can be used for various sizes of medical instruments). But in some cases, a particular base 310 can be coupled with two or more sizes of medical instruments, in a manner that is analogous to the universal cap 330 as described above.

In FIG. 8A, the universal cap 330 is coupled to the base 310 and in the open unlatched position. Projections 316 and 317 are oriented generally vertically and spaced apart from each other to define the catheter receiving channel 320. The orientation of the projections 316 and 317 shown is an unconstrained orientation of the projections 316 and 317. That is, when the universal cap 330 is not in contact with the projections 316 and 317, the projections 316 and 317 will be biased generally to the orientation as shown. In such an orientation, a user can readily engage the catheter 20 within the catheter receiving channel 320.

In this embodiment, the projection 316 has a substantially greater height than the projection 317, and at least the projection 316 is reliantly flexible. The projection 316 is positioned closer to the projection 331 of the cap 330 so that the cap 330 will engage the flexible projection 316 during the process of fully securing to the base 310. As the cap 330 is pivoted onto the base 310, an inner cap surface 332 contacts and bears against the longer projection 316 such that the extra length of projection 316 is deflected over an upper aspect of the catheter 20, thereby providing a frictional grip along the exterior of the catheter 20.

FIG. 8B shows the cap 330 in its latched position on the base 310. The longer projection 316 has been deflected or folded-over onto the exterior of the catheter 20. The pivoting motion of the cap 330 has made the inner cap surface 332 deflect the longer projection 316 toward the shorter projection 317 and onto the catheter 20. In this arrangement, the catheter is lightly compressed within the catheter receiving channel 320 by the downward pressure from the longer projection 316 and inner cap surface 332. The compressibility and tackiness of the catheter engagement portion 315 allows the anchor device 300 to firmly restrain the catheter 20 from sliding in relation to the catheter receiving channel 320, while reducing the likelihood of "pinching" or occluding the catheter 20.

Figure 9:
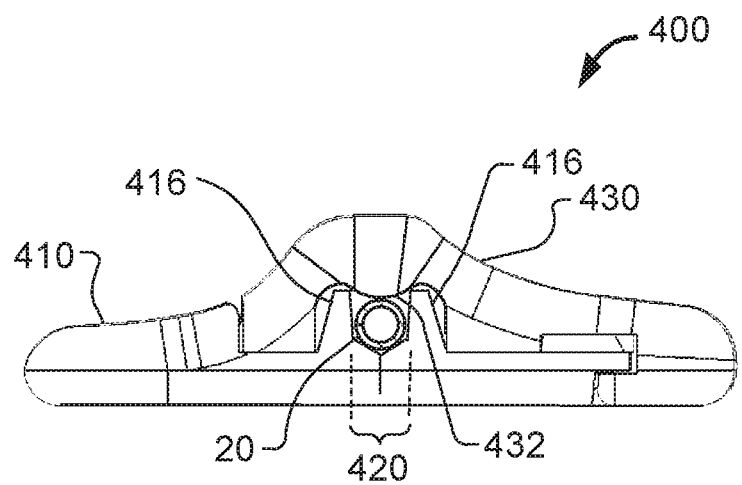
FIG. 9 is a rear view of an anchor device with another example universal cap, in accordance with some embodiments.
Figure 10:
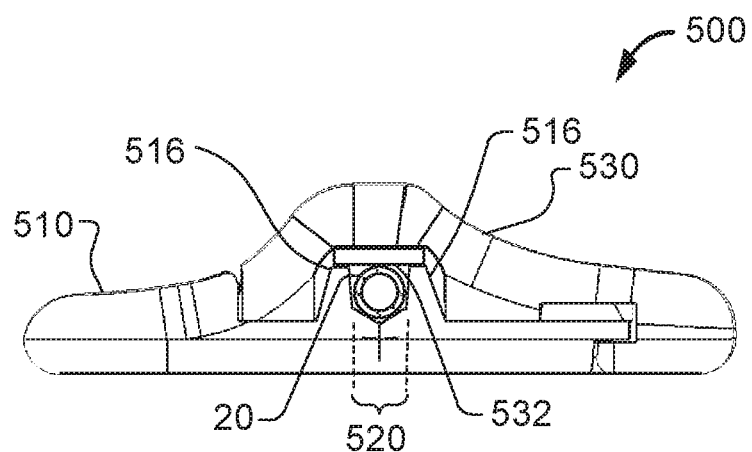
FIG. 10 is a rear view of an anchor device with another example universal cap, in accordance with some embodiments.

Referring now to FIGS. 9 and 10, some embodiments of anchor devices described herein can be equipped with cap devices having different structures configured to engage the catheter 20 or other medical instrument in the channel of the corresponding base. For example, anchor devices 400 and 500 that include two additional embodiments of universal caps 430 and 530, respectively. The bases 410 and 510 of the anchor devices 400 and 500 are similar to the base 210 previously described in connection with FIGS. 6 and 7A-7B. That is, the bases 410 and 510 include projections 416 and 516 respectively that define the catheter receiving channels 420 and 520, respectively.

As shown in FIG. 9, some embodiments of the cap 430 can include a convex protrusion 432 on the underside of the universal cap 430, which is configured to retain an upper aspect of the catheter 20 in its position (e.g., prevent upward motion of the catheter 20 away from the channel 420) so that the catheter 20 resides in the channel 420. In this embodiment, the protrusion 432 can optionally contact with the catheter 20 when the catheter 20 is within the catheter receiving channel 420 and the universal cap 430 is latched on the base 410. In such circumstances, the protrusion 432 exerts a light force on the catheter 20 to restrain the catheter 20 within the catheter receiving channel 420, while not exerting enough force to "pinch" or occlude the catheter 20. In this manner, the anchor device 400 and the catheter 20 can be securely coupled together.

As shown in FIG. 10, some embodiments of the cap 530 can include a flexible pad 532 on the underside of the universal cap 530. The pad 532 can be comprised of a soft durometer material such as the same material comprising the projections 516, or a dissimilar material. The pad 532 can optionally contact with the catheter 20 when the catheter 20 is within the catheter receiving channel 520 and the universal cap 530 is latched on the base 510. In such circumstances, the pad 532 can exert a light force on the catheter 20 to restrain the catheter 20 within the catheter receiving channel 520, while not exerting enough force to "pinch" or occlude the catheter 20. In this manner, the anchor device 500 and the catheter 20 can be securely coupled together.

From the foregoing description, it can be understood from all three examples of the cap embodiments 330, 430, and 530, that the cap can function as part of an anchor device to secure any of a variety of differently sized catheters or other medical instruments to a selected base. In other words, caps 330, 430, and 530 can be used with any one of a variety of differently sized anchor device bases, which include differently sized channels or other structures specifically configured to couple with a range of different sizes of medical instruments. Further, in some embodiments the bases themselves (in addition to the universal caps 330, 430, and 530) can be used with a range of different sizes of medical instruments.

A number of embodiments of the invention have been described. Nevertheless, it will be understood that various modifications may be made without departing from the scope of the invention. Accordingly, other embodiments are within the scope of the following claims.

What is claimed is:

1. A method of using a medical anchor system, comprising: advancing an anchor device toward a skin penetration point of a user while the anchor device is in a folded condition so that a plurality of subcutaneous tines of the anchor device are generally adjacent to each other; inserting the subcutaneous tines through the skin penetration point and into a subcutaneous region adjacent to an underside of a skin layer while the anchor device is in the folded condition; adjusting the anchor device to a non-folded condition after the subcutaneous tines are inserted into the subcutaneous layer so that subcutaneous tines are in an anchored position different from the folded condition; and securing a medical instrument to the anchor device, wherein securing the medical instrument comprises pivoting a cap of the anchor device in relation to a retainer base of the anchor device about a pivot axis defined by connection between the retainer base and the cap during adjustment between a first arrangement and a second arrangement, wherein the medical instrument is received in a channel that is defined between the cap and the retainer base when the cap and the retainer base are in the first arrangement, and wherein the cap is removable from the medical instrument when the cap and the retainer base are in the second arrangement.

2. The method of claim 1, wherein pivoting the cap in relation to the retainer base comprises pivoting about the pivot axis defined by a cooperative engagement of a projection on the cap and a slot on the retainer base.

3. The method of claim 1, wherein pivoting the cap in relation to the retainer base comprises pivoting about the pivot axis defined by a cooperative engagement of a slot on the cap and a projection on the retainer base.

4. The method of claim 1, wherein in the folded condition the plurality of subcutaneous tines of the anchor device are oriented to extend in substantially the same direction.

5. The method of claim 4, wherein in the non-folded condition the subcutaneous tines extend generally away from one another.

6. The method of claim 1, wherein securing the medical instrument to the anchor device occurs after the subcutaneous tines are adjusted to the anchored position.

7. The method of claim 6, further comprising inserting the medical instrument through the skin penetration point of a user.

8. The method of claim 7, wherein inserting the medical instrument occurs before inserting the subcutaneous tines.

9. The method of claim 1, wherein securing the medical instrument to the anchor device comprises configuring the cap and the retainer base in a latched arrangement, wherein the latched arrangement comprises an arrangement wherein the cap is mechanically retained in a stationary position in relation to the retainer base.

10. The method of claim 9, further comprising adjusting the cap to an unlatched arrangement in which the cap is released from the retainer base, wherein the cap is transitioned between the latched and unlatched arrangements by applying a manual force simultaneously to the cap and the retainer base.

11. The method of claim 10, wherein the retainer base comprises a first tab including an exposed surface and the cap includes a second tab including an exposed surface, and the manual force is applied simultaneously to the first tab and the second tab.

12. A method of using a medical anchor system, comprising: advancing an anchor device toward a skin penetration point of a user while the anchor device is in a folded condition so that a plurality of subcutaneous tines of the anchor device are generally adjacent to each other; inserting the subcutaneous tines through the skin penetration point and into a subcutaneous region adjacent to an underside of a skin layer while the anchor device is in the folded condition; adjusting the anchor device to a non-folded condition after the subcutaneous tines are inserted into the subcutaneous layer so that subcutaneous tines are in an anchored position different from the folded condition; and securing a medical instrument to the anchor device, wherein securing the medical instrument comprises pivoting a cap of the anchor device in relation to a retainer base of the anchor device about a pivot axis defined by connection between the retainer base and the cap, wherein the medical instrument is received in a channel that is defined between the cap and the retainer base; wherein the cap comprises a first connector at the location of connection with the retainer base, and a second connector that is fixedly positioned relative to the first connector such that the first and second connectors are spaced a fixed distance when the cap is pivoted about the pivot axis.

13. The method of claim 12, wherein securing the medical instrument to the anchor device comprises configuring the cap and the retainer base in a latched arrangement, wherein the latched arrangement comprises an arrangement wherein the cap is mechanically retained in a stationary position in relation to the retainer base.

14. A method of using a medical anchor system, comprising: advancing an anchor device toward a skin penetration point of a user while the anchor device is in a folded condition so that a plurality of subcutaneous tines of the anchor device are generally adjacent to each other; inserting the subcutaneous tines through the skin penetration point and into a subcutaneous region adjacent to an underside of a skin layer while the anchor device is in the folded condition; adjusting the anchor device to a non-folded condition after the subcutaneous tines are inserted into the subcutaneous layer so that subcutaneous tines are in an anchored position different from the folded condition; and securing a medical instrument to the anchor device after the subcutaneous tines are adjusted to the anchored position, wherein securing the medical instrument comprises pivoting a cap of the anchor device in relation to a retainer base of the anchor device about a pivot axis defined by connection between the retainer base and the cap during adjustment between a first arrangement and a second arrangement, wherein the medical instrument is received in a channel that is defined between the cap and the retainer base when the cap and the retainer base are in the first arrangement, and wherein the cap is removable from the medical instrument when the cap and the retainer base are in the second arrangement.

15. The method of claim 14, wherein the retainer base comprises a first tab including an exposed surface, and the cap includes a second tab including an exposed surface.

16. The method of claim 15, further comprising adjusting the cap to an unlatched arrangement in which the cap is released from the retainer base, wherein the cap is transitioned between the latched and unlatched arrangements by applying a manual force simultaneously to the first tab and the second tab.

17. The method of claim 16, wherein the cap comprises a first connector at the location of connection with the retainer base, and a second connector that is fixedly positioned relative to the first connector such that the first and second connectors are spaced a fixed distance when the cap is pivoted about the pivot axis.

18. The method of claim 17, wherein in the folded condition the plurality of subcutaneous tines of the anchor device are oriented to extend in substantially the same direction, and in the non-folded condition the subcutaneous tines are orient to extend generally away from one another.

19. The method of claim 18, further comprising inserting the medical instrument through the skin penetration point of a user, wherein inserting the medical instrument occurs before inserting the subcutaneous tines.

20. The method of claim 19, wherein securing the medical instrument to the anchor device comprises configuring the cap and the retainer base in a latched arrangement, wherein the latched arrangement comprises an arrangement wherein the cap is mechanically retained in a stationary position in relation to the retainer base.

* * * * *